United States Patent [19]

Camaggi et al.

[11] Patent Number: 4,702,762
[45] Date of Patent: Oct. 27, 1987

[54] METHOD OF PROTECTING CULTIVATIONS OF AGRARIAN INTEREST FROM THE ACTION OF NONSELECTIVE HERBICIDES

[75] Inventors: Giovanni Camaggi, Lodi; Franco Gozzo, San Donato Milanese; Ernesto Signorini, Malnate; Ottorino Palla, Crema, all of Italy

[73] Assignee: Montedison S.p.A., Milan, Italy

[21] Appl. No.: 731,389

[22] Filed: May 7, 1985

Related U.S. Application Data

[63] Continuation of Ser. No. 475,959, Mar. 16, 1983, abandoned.

[30] Foreign Application Priority Data

Mar. 19, 1982 [IT] Italy ............................... 20272 A/82

[51] Int. Cl.$^4$ ........................................... A01N 25/32

[52] U.S. Cl. .......................................... 71/90; 47/57.6; 71/100; 71/118; 541/201

[58] Field of Search ........................... 71/90, 100, 118; 47/57.6

[56] References Cited

U.S. PATENT DOCUMENTS

| | | | |
|---|---|---|---|
| 4,319,031 | 3/1980 | Teach | 71/90 |
| 4,371,389 | 2/1983 | Howe et al. | 71/90 |
| 4,437,876 | 3/1984 | Howe et al. | 71/90 |

*Primary Examiner*—Catherine L. Mills
*Attorney, Agent, or Firm*—Stevens, Davis, Miller & Mosher

[57] ABSTRACT

A method of protecting useful cultivations from the toxic action of nonselective herbicides, consisting in using, as antidotes, 2- or 4-thiazolidine-carboxylic acids and derivatives thereof.

11 Claims, No Drawings

METHOD OF PROTECTING CULTIVATIONS OF AGRARIAN INTEREST FROM THE ACTION OF NONSELECTIVE HERBICIDES

This is a continuation of application Ser. No. 475,959, filed Mar. 16, 1983, now abandoned.

BACKGROUND OF THE INVENTION

The herbicides belonging to the class of chloroacetanilides or of thiolcarbamates are very useful compounds in the fight against the weeds infesting agrarian cultivations.

Many of these herbicides, however, exert their toxic action also towards certain useful cultivations such as, for example, maize and sorghum, and, by consequence, being not selective, they cannot be used for the weed-killing of such cultivations.

The availability of antidotes, i.e. of compounds which protect the useful cultivations from the action of the herbicides without contemporaneously reducing their herbicide action towards the infesting plants, permits to make use of these herbicides also for defending those useful cultivations which otherside would be damaged.

Among the main herbicides which prove to be phytotoxic for certain useful cultivations there are those belonging to the class of the chloroacetanilides comprising, for example, N-methoxymethyl-2,6-diethyl-chloroacetanilide (common name: Alachlor), N-butoxymethyl-2,6-diethyl-chloroacetanilide (common name: Butachlor), N-methoxyethyl-2-methyl-6-allyl-chloroacetanilide and the ones belonging to the class of the thiolcarbamates comprising, e.g., N,N-diiaopropyl-S-(2,3-dichloroallyl)-thiolcarbamate (common name: Diallate); N,N-diisopropyl-S-(2,3,3-trichloroallyl)-thiolcarbamate (common name: Triallate); N,N-diethyl-S-(4-chlorobenzyl)-thiolcarbamate (common name: Benthiocarb); N,N-dipropyl-S-ethyl-thiolcarbamate (common name: Eptam).

Compounds belonging to different chemical classes are known, which are capable of protecting useful cultivations from the toxic action exerted by the herbicides. For example, dichloroacetamides useful as antidotes have been described in U.S. Pat. No. 4,021,224 (Stauffer) or in U.S. Pat. No. 4,228,101 (Montedison S.p.A.). 2-chloro-thiazoles disubstituted in positions 4,5, which are useful as antidotes in the defence of sorghum cultivations have been described in European patent application No. 27019 (Monsanto Co.).

THE PRESENT INVENTION

We have now found that the toxic action of nonselective herbicides, belonging e.g. to the class of the chloroacetanilides and of the thiolcarbamates, towards useful cultivations can be sensibly reduced or eliminated, without decreasing, at the same time, the herbicide action towards infesting plants if use is made, as antidotes, of compounds of formula:

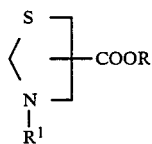

wherein:

group COOR is in position 2 or 4 in the thiazolidine ring, R represents a hydrogen atom or an alkyl $C_1$–$C_4$; $R^1$ represents a hydrogen atom, an acetyl group optionally substituted by 1 to 3 halogen atoms.

Thus, an object of the present invention consists in providing a method of reducing the damages towards useful cultivations caused by nonselective herbicides belonging, for example, to the class of the chloroacetanilides or of the thiolcarbamates, such method consisting in treating the seeds, the plants or the soil in which they grow with an effective amount of an antidote of formula I, either as such or in the form of a suitable composition.

Another object of the present invention are the compositions containing a compound of formula I as an active ingredient along with inert vehicles and optionally other additives useful to treat the seeds of useful plants, the plants themselves or the soil in which they grow.

A further object of this invention are the seeds of useful plants treated with an effective amount of a compound of formula I.

The compounds of formula I may also be in the form of salts, e.g. hydrochlorides, when in formula I $R^1$=H.

For the uses according to this invention, the individual compounds of formula I, also in admixture with one another, and the corresponding salts are equally valid.

Some of the compounds of formula I are known, namely:

2-thiazolidine-carboxylic acid and the lower alkyl esters thereof, 4-thiazolidine-carboxylic acid and the lower alkyl esters thereof, N-acetyl-2-thiazolidine-carboxylic acid, the methyl ester of N-dichloroacetyl-4-thiazolidine-carboxylic acid, N-acetyl-4-thiazolidine-carboxylic acid.

Some of these known compounds, such as the derivatives of 4-thiazolidine-carboxylic acid, are useful as biostimulants for agrarian uses. The others have been tested in the pharmaceutical field as hepatoprotectors or intermediates for antibiotics.

As far as we know, these compounds were never supposed to be associated with properties of antidotes for herbicides.

The new compounds of formula I are easily preparable by acylation of 2- or 4-thiazolidine-carboxylic acid or of the respective alkyl esters with the proper haloacetyl chloride, in an inert solvent and in the presence of a halogenhydric acid-accepting base.

As an alternative, acylation can be accomplished by substituting the acyl halide by the corresponding anhydride.

The following compounds:

N-dichloroacetyl-2-thiazolidine-carboxylic acid

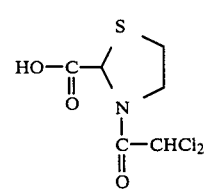

[melting point=136°–140° C.; IR (cm$^{-1}$): 1710 ($\gamma$COOH), 1660 ($\gamma$CO—N)], methyl ester of N-dichloroacetyl-2-thiazolidine-carboxylic acid

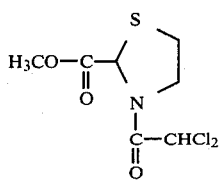

[melting point=80°-81° C.; IR (cm$^{-1}$): 1740 ($\gamma$COOCH$_3$), 1670 ($\gamma$CO—N)] are new and represent, as such, a further object of this invention.

It has been furthermore observed that N-acetyl-2-thiazolidine-carboxylic acid and the esters thereof with alcohols $C_1$-$C_4$ possess, besides antidotic properties, also biostimulating properties.

The action of these compounds, when employed as biostimulants, result in a more luxuriant aspect of the plants and in an increase in a harvest.

Thus, a further object of the present invention resides in the use of N-acetyl-2-thiazolidine-carboxylic acid and of its esters with alcohols $C_1$-$C_4$ as biostimulants for cultivations of agrarian interest.

As mentioned hereinbefore, the antidotes of formula I can be applied to the useful cultivations according to various modalities.

For example, they can be utilized for a preventive treatment of seeds, so that the plants developing therefrom will be protected from the toxic action exerted by nonselective herbicides.

As an alternative, the compounds of formula I are employable for treating the plant itself or the soil in which it grows. In this case, the antidotes can be distributed alone or in combination with the nonselective herbicides.

The different types of applications require different conditions which affect the practical aspects of the treatment, such as antidote amount, period of treatment and type of composition.

Other factors influencing the practical aspects of the treatment are the type of cultivation to be protected, the nonselective herbicide employed, the climatic and environmental conditions.

When the antidote is applied in a preventive seed treatment, it is employable as such or, preferably, as a proper composition.

The compositions for the treatment of the seeds may be in the form of powders, wettable powders or emulsifiable concentrates, and generally consist of the active compound in amounts ranging from 0.5 to 95% by weight and of the usual inert vehicles which, depending on the composition type, may be solid, such as talc, silica, diatomite, bentonite, calcium carbonate and mixtures thereof, or liquid, such as water, alkyl-aromatic hydrocarbons, acetone, cyclohexanone and mixtures thereof.

The compositions may also contain suitable additives, such as surfactants, wetting agents, dispersants and mixtures thereof.

As previously cited, the antidote amount to be distributed on the seeds varies as a function of various factors; however, it is generally sufficient to use product amounts ranging from 0.1 to 100 g/Kg of seeds.

The treatments directly effected on the plant or in the medium where the plant grows require, of course, that the antidote be used in the form of a suitable composition according to the usual practice for this kind of application.

In the applications in which the antidote is distributed on the vegetation or into the soil along with the nonselective herbicide in a single formulation, the type of formulation and the content vary both as a function of the above-mentioned factors, and as a function of the herbicide type utilized and of the characteristics thereof.

The antidote amount to be used ranges from 0.1 to 10 Kg/ha and the ratio between antidote and herbicide in the composition may range from 1:5 to 5:1.

The following examples are given to better illustrate the present invention.

EXAMPLE 1

Antidotic activity in maize plants by preventive treatment of the seeds

General modalities:

60 maize seeds were treated with 60 or 120 mg of the antidote to be tested, dissolved in 3 ml of an aqueous solution of dimethylsulphoxide (DMSO) at 3% by weight, or in 3 ml of water optionally containing a wetting agent at 0.1%.

On a basis of 60,000 seeds/ha, the dose employed was corresponding to 60 or to 120 g of antidote per hectare, or corresponding to 2.8 or 5.6 g of antidote per Kg. of seeds.

The treatment was accomplished by mixing the seeds for 10 minutes in said solution and then by allowing them to dry during 24 hours, stirring them at intervals in the course of the first hours.

The treated seeds were then sown in ground previously treated with the weed-killer being tested, at a predetermined dose. As a control, also maize seeds left in a water bath not containing any antidote, under the same conditions, were sown.

After a 10-day growth under continuous light and at a temperature of 25° C., the antidotic activity was evaluated by comparing the growth of the plants treated with the weed-killer and with the weed-killer plus the antidote, with the growth of the plants treated neither with the weed-killer nor with the antidote. In the antidotic activity tests, the following compounds of formula I were tested:

A=N-acetyl-4-thiazolidine-carboxylic acid
B=4-thiazolidine-carboxylic acid
C=2-thiazolidine-carboxylic acid
D=N-acetyl-2-thiazolidine-carboxylic acid
E=methyl ester of N-dichloroacetyl-4-thiazolidine-carboxylic acid
F=N-dichloroacetyl-2-thiazolidine-carboxylic acid
G=methyl ester of acid C
H=methyl ester of acid F
I=methyl ester of N-chloroacetyl-4-thiazolidine-carboxylic acid.

The herbicides employed were Alachlor (chloroacetanilide) and Eptam (thiocarbamate).

The results recorded on following Tables 1 and 2 refer to the toxic action of the herbicide in the presence of the antidote on the maize plants and are expressed according to a scale of values from 4 (complete stop of growth or death of the plant) to 0 (plant growth like that of plants not treated with herbicide and antidote).

As a consequence, an evaluation equal to that of the herbicide alone is indicative of the absence of an antidotic effect, while lower values are indicative of an antidotic effect increasing towards the lower values.

Preliminary laboratory tests proved that the antidotes of formula I are not toxic for maize and that the herbicide activity of Alachlor and Eptam towards the common infesting plants of maize (*Solanum nigrum, Amarantus* spp., *Echinochloa* spp., *Digitaria* Spp., *Setaria* spp., *Sorghum halepense, Panichum dichotomiflorum, Cyperus rotundus, Cyperus esclulantus*) is not affected by the presence of the antidote in this kind of tests.

TABLE 1

Antidotic activity by preventive treatment of maize seeds.
Herbicide: Alachlor.

| Antidote | g of antidote/1000 g of seeds | Antidote solution | Toxic action on maize exerted by the herbicide a dose of: | |
|---|---|---|---|---|
| | | | 16 Kg/ha | 8 Kg/ha |
| — | — | — | 3 | 3 |
| A | 2.8 | H₂O | 2 | 2 |
| B | 2.8 | H₂O | 2-3 | 2-3 |
| C | 2.8 | H₂O | 1 | 1 |
| D | 2.8 | H₂O | 2 | 1 |
| E | 2.8 | H₂O/DMSO 3% | 2 | 1 |
| F | 2.8 | H₂O/DMSO 3% | 1 | 0 |
| G | 2.8 | H₂O/DMSO 3% | 2 | 1 |
| H | 2.8 | H₂O/DMSO 3% | 1-2 | 0 |

TABLE 2

Antidotic activity by preventive treatment of maize seeds.
Herbicide: Eptam.

| Antidote | g of antidote/1000 g of seeds | Antidote solution (1) | Toxic action on maize exerted by the weed-killer at a dose of: | |
|---|---|---|---|---|
| | | | 4 Kg/ha | 2 Kg/ha |
| — | — | — | 3 | 2 |
| C | 2.8 | H₂O/DMSO 3% | 2 | 1 |
| C | 5.6 | H₂O/DMSO 3% | 1 | 0 |
| C | 2.8 | H₂O/wetting agent 0.1% | 1 | 0 |
| C | 5.6 | H₂O/wetting agent 0.1% | 1 | 0 |
| C | 2.8 | H₂O/wetting agent 0.5% | 0 | 0 |
| G | 2.8 | H₂O/DMSO 3% | 2 | 1 |
| F | 2.8 | H₂O/DMSO 3% | 0 | 0 |
| H | 2.8 | H₂O/DMSO 3% | 0 | 0 |
| I | 2.8 | H₂O/DMSO 3% | 2-3 | 1 |

Notes to Table 2
(1) As a wetting agent there was indifferently utilized "Tween 20" (registered trade-mark of Atlas Co. for sorbitane monolaurate polyoxyethylated with 20 moles of ethylene oxide per mole of substrate) or "Emulson 20 OM" (registered trademark of ROL Co. for sorbitane oleate polyoxyethylated with 20 moles of ethylene oxide per mole of substrate).

What we claim is:

1. A method of reducing the damage caused to maize cultivations due to the application thereto of alachlor or eptam herbicides belonging, respectively, to the class of chloroacetanilides and of thiolcarbamates which comprises treating maize seeds, with an antidotally effective amount of a compound having the following formula:

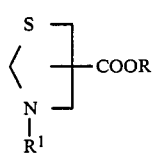
(I)

wherein the —COOR group is in position 2 or 4 in the thiazolidine ring, R is a hydrogen atom or a $C_1$–$C_4$ alkyl, and $R^1$ is selected from the group consisting of a hydrogen atom, an acetyl group and an acetyl group substituted by 1 to 3 halogen atoms.

2. The method according to claim 1, characterized in that the antidote of formula I is employed in the form of a composition suitable for agrarian use.

3. The method according to claim 1, characterized in that the antidote of formula I is employed in the preventive treatment of maize seeds.

4. Maize seeds treated with an antidotally effective amount of a compound having the following formula:

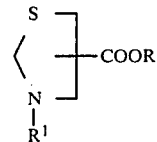

wherein the —COOR group is in position 2 or 4 in the thiazolidine ring, R is a hydrogen atom or a $C_1$–$C_4$ alkyl, and $R^1$ is selected from a group consisting of a hydrogen atom, an acetyl group and an acetyl group substituted by 1 to 3 halogen atoms.

5. Maize seeds treated with an antidotally effective amount of N-dichloroacetyl 2-thiazolidine-carboxylic acid.

6. Maize seeds treated with an antidotally effective amount of the methyl ester of N-dichloroacetyl-2-thiazolidine-carboxylic acid.

7. Maize seeds treated with a herbicidally effective amount of alachlor herbicide and an antidotally effective amount of a compoiund of the following formula:

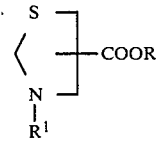

wherein the —COOR group is in position 2 or 4 in the thiazolidine ring, R is a hydrogen atom or a $C_1$–$C_4$ alkyl, and $R^1$ is selected from a hydrogen atom, an acetyl group, and an acetyl group substituted by 1 to 3 halogen atoms.

8. Maize seeds treated with a herbicidally effective amount of eptam herbicide and an antidotally effective amount of a compound of the following formula:

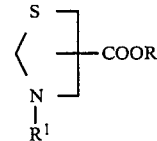

wherein the —COOR group is in position 2 or 4 in the thiazolidine ring, $R^1$ is a hydrogen atom or a $C_1$–$C_4$ alkyl, and $R^1$ is selected from the group consisting of a hydrogen atom, an acetyl group, and an acetyl group substituted by 1 to 3 halogen atoms.

9. Maize seeds treated with a herbicidally effective amount of alachlor herbicide and an antidotally effective amount of N-dichloroacetyl-2-thiazolidine-carboxylic acid.

10. Maize seeds treated with a herbicidally effective amount of eptam herbicide and an antidotally effective amount of N-dichloroacetyl-2-thiazolidine-carboxylic acid.

11. Maize seeds treated with a herbicidally effective amount of alachlor herbicide and an antidotally effective amount of the methyl ester of N-dichloroacetyl-2-thiazolidine-carboxylic acid.

* * * * *